United States Patent [19]

Chu

[11] Patent Number: 4,687,770

[45] Date of Patent: Aug. 18, 1987

[54] ISOXAZOLO-PYRIDO-BENZOXAZINE AND ISOTHIAZOLO-PYRIDO-BENZOXAZINE DERIVATIVES

[75] Inventor: Daniel T. Chu, Vernon Hills, Ill.

[73] Assignee: Abbott Laboratories, North Chicago, Ill.

[21] Appl. No.: 919,045

[22] Filed: Oct. 15, 1986

Related U.S. Application Data

[63] Continuation-in-part of Ser. No. 812,560, Dec. 23, 1985, abandoned.

[51] Int. Cl.[4] .................. A61K 31/535; A61K 31/54; C07D 498/14
[52] U.S. Cl. .................................... 514/211; 514/212; 514/218; 514/222; 514/229; 514/234; 540/544; 540/553; 540/599; 540/575; 544/47; 544/58.6; 544/73; 544/99
[58] Field of Search ............... 540/544, 575, 553, 599; 544/58.6, 99, 47, 73; 514/211, 218, 222, 229, 234, 212

[56] References Cited

U.S. PATENT DOCUMENTS

| 3,149,104 | 9/1964 | Lesher et al. | 260/240 |
|---|---|---|---|
| 4,017,622 | 4/1977 | Minami | 424/250 |
| 4,146,719 | 4/1979 | Irikura | 544/363 |
| 4,284,629 | 8/1981 | Grohe et al. | 544/58.6 X |
| 4,382,892 | 5/1983 | Hayakawa et al. | 544/73 X |
| 4,415,572 | 11/1983 | Tominaga et al. | 544/360 X |
| 4,429,127 | 1/1984 | Irikura et al. | 544/363 |
| 4,439,436 | 3/1984 | Wentland et al. | 546/90 X |
| 4,443,447 | 4/1984 | Gerster et al. | 544/101 X |
| 4,473,568 | 9/1984 | Hutt, Jr. | 544/58.6 X |
| 4,540,694 | 9/1985 | Chu | 544/99 X |
| 4,542,133 | 9/1985 | Chu | 544/99 X |

FOREIGN PATENT DOCUMENTS

| 0009425 | 4/1980 | European Pat. Off. |
| 0078362 | 5/1983 | European Pat. Off. |
| 2362553 | 12/1973 | Fed. Rep. of Germany |
| 2338325 | 2/1974 | Fed. Rep. of Germany |
| 2341146 | 2/1974 | Fed. Rep. of Germany |
| 3142854 | 5/1983 | Fed. Rep. of Germany |
| 5128764 | 8/1981 | Japan |
| 1147336 | 4/1969 | United Kingdom |
| 2034698 | 11/1972 | United Kingdom |

OTHER PUBLICATIONS

Sato et al, "In Vitro and In Vivo Activity of DL-8280, A New Oxazine Derivative", *Antimicrobial Agents and Chemotherapy*, vol. 22, No. 4, pp. 548–553, Oct. 1982.

Koga et al., "SAR of Substituted Quinoline-3-Carboxylic Acids", *Journal of Medicinal Chemistry*, 1980, vol. 23, No. 12, p. 1358.

*Primary Examiner*—Richard L. Raymond
*Attorney, Agent, or Firm*—Martin L. Katz; Robert W. Stevenson

[57] ABSTRACT

This invention relates to novel isoxazolo-pyrido-benzoxazine and isothiazolo-pyrido-benzoxazine derivatives having antibacterial properties.

8 Claims, No Drawings

ISOXAZOLO-PYRIDO-BENZOXAZINE AND ISOTHIAZOLO-PYRIDO-BENZOXAZINE DERIVATIVES

This application is a continuation-in-part of application Ser. No. 812,560 filed Dec. 23, 1985 entitled Isoxazolo-Pyrido-Benzoxazine and Isothiazolo-Pyrido-Benzoxazine Derivatives, now abandoned.

This invention relates to novel antibacterial agents and, more particularly, to benzoxazine derivatives having the formula:

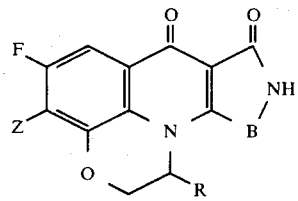

which may exist in its tautomer form (II).

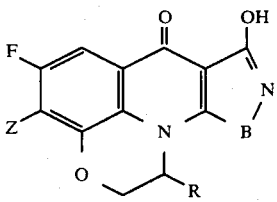

wherein B is oxygen or sulfur; and R is $C_1$ to $C_4$ alkyl and a methylene in which the formula of this molecule will be represented as (III).

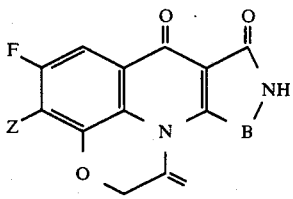

Z is an amino group having the formula:

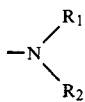

wherein $R_1$ is hydrogen, $C_1$ to $C_4$ alkyl, or hydroxy-substituted $C_1$ to $C_4$ alkyl and $R_2$ is $C_1$ to $C_4$ alkyl, hydroxy-substituted $C_1$ to $C_4$ alkyl, an amino group, mono-$(C_1$-$C_4)$ alkylamino or di-$(C_1$-$C_4)$ alkylamino.

Alternatively, Z can be aliphatic heterocyclic ring containing 5 to 7 atoms, containing 1 or 2 hetero atoms which are selected from the group consisting of S, O, N and combinations thereof, with the remaining atoms in the aliphatic heterocyclic ring being carbon atoms, as well as substituted derivatives thereof. The aliphatic heterocyclic ring preferably has the formula:

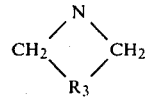

wherein $R_3$ is selected from the group consisting of the formula —$(CH_2)_n$— wherein n=2 or 3 and a group of the formula —$(CH_2)_n$—$R_4$—$CH_2$— wherein n=1 or 2 and $R_4$ is selected from the group consisting of —S—, —O—, and —N—. Also included are substituted derivatives of such heterocyclic rings wherein the substituent is one or more of a $C_1$ to $C_4$ alkyl group, hydroxy-substituted $C_1$ to $C_4$ alkyl, phenyl or halophenyl, amino-substituted $C_1$ to $C_4$ alkyl, hydroxy, halogen, alkanoylamido containing 1 to 4 carbon atoms, an amine group having the formula:

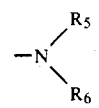

wherein $R_5$ and $R_6$ are each independently selected from the group consisting of hydrogen or $C_1$ to $C_4$ alkyl.

Illustrative of such heterocyclic groups are piperazinyl groups, piperidinyl groups, pyrrolidinyl groups, morpholino groups, thiomorpholino groups and homopiperazinyl groups (i.e., hexahydro-1-H-1,4-diazepinyl).

Alternatively, Z can also be a bicyclic heterocyclic ring having the formula

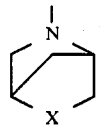

where X is selected from the group consisting of —S—, —O—, and —N—. Also included are substituted bicyclic heterocyclic ring wherein the substituent is one or more of $C_1$ to $C_4$ alkyl group, hydroxy-substituted $C_1$ to $C_4$ alkyl, phenyl or halophenyl, amino-substituted $C_1$ to $C_4$ alkyl, hydroxy, halogen, alkanoylamido containing 1 to 4 carbon atoms, an amine group having the formula:

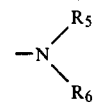

wherein $R_5$ and $R_6$ are each independently selected from the group consisting of hydrogen or $C_1$ to $C_4$ alkyl.

Z can also be a phenyl which may be substituted by one to three substituents selected from alkyl of 1 to 4 carbon atoms, alkylsulfonyl of 1 to 4 carbon atoms, fluoro, chloro, hydroxy, hydroxyalkyl of 1 to 3 carbon atoms, amino, alkylamino of 1 to 4 carbon atoms, aminoalkyl of 1 to 3 carbon atoms and aminosulfonyl.

AS used herein, the term "$C_1$ to $C_4$ alkyl" refers to branched or straight chain lower alkyl groups including methyl, ethyl, propyl isopropyl, butyl, etc.

The term "halogen" refers to chloro, bromo, fluoro and iodo groups.

The term "amino" refers to —$NH_2$.

The term "alkanoylamido" refers to a substituent of the formula $R_7$

wherein $R_3$ is $C_1$ to $C_3$ alkyl, and includes but is not limited to acetylamino.

The preferred compound of the invention are those having the formula:

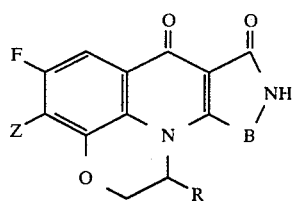

where B is selected from oxygen and sulfur; R is methyl or methylene (structure III) and Z is piperazinyl or substituted piperazinyl or aminopyrrolidinyl, substituted pyrrolidinyl or substituted aminopyrrolidinyl as described above.

The chiral centers of the compounds of the invention may be either the "R" or "S" configuration.

Representative of such preferred compounds wherein B is oxygen are 1-methyl-4-(1-piperizinyl)-5-fluoro-1,2,8,9-tetrahydro-7H-isoxazolo[4',5':5,6-]pyrido[1,2,3-de][1,4]benzoxazine-7,8-dione, 1-methyl-4-(4-methyl-1-piperazinyl)-5-fluoro-1,2,8,9-tetrahydro-7H-isoxazolo[4',5':5,6]pyrido[1,2,3-de][1,4]benzoxazine-7,8-dione, 1-methyl-4-(3-amino-1-pyrrolidinyl)-5-fluoro-1,2,8,9-tetrahydro-7H-isoxazolo[4',5':5,6-]pyrido[1,2,3-de][1,4]benzoxazine-7,8-dione, 1-methyl-4-(3-methyl-1-piperazinyl)-5-fluoro-1,2,8,9-tetrahydro-7H-isoxazolo[4',5':5,6]pyrido[1,2,3-de][1,4]benzoxazine-7,8-dione, 1-methyl-4-(3-amino-4-methyl-1-pyrrolidinyl)-5-fluoro-1,2,8,9-tetrahydro-7H-isoxazolo[4',5':5,6]pyrido[1,2,3-de] [1,4]benzoxazine-7,8-dione, 1-methyl-4-(2-methyl-1-piperazinyl-5-fluoro-1,2,8,9-tetrahydro-7H-isoxazolo[4',5':5,6]pyrido[1,2,3-de][1,4]benzoxazine-7,8-dione, 1-methyl-4-(-3-methyl-3-aminopyrrolidin-1-yl)-5-fluoro-1,2,8,9-tetrahydro-7H-isoxazolo[4',5':5,6]pyrido[1,2,3-de][1,4]benzoxazine-7,8-dione, 1-methyl-4-(2-methyl-4-aminopyrrodin-1-yl)-5-fluoro-1,2,8,9-tetrahydro-7H-isoxazolo[4',5':5,6-]pyrido[1,2,3-de][1,4]benzoxazine-7-8-dione, 1-methyl-4-(2-(2,5-diazabicyclo[2.2.1]heptyl)-5-fluoro-1,2,8,9-tetrahydro-7H-isoxazolo[4',5':5,6[pyrido[1,2,3-de][1,4-]benzoxazine-7,8-dione, 1-methyl-4-(3-N'-ethylamino methyl-pyrrolidin-1-yl)5-fluoro-1,2,8,9-tetrahydro-7H-isoxazolo-[4'5':5,6]pyrido[1,2,3-de][1,4]benzoxazine-7,8-dione, 1-methylene-4-(1-piperazinyl)-5-fluoro-1,2,8,9-tetrahydro-7H-isoxazolo[4',5':5,6]pyrido[1,2,3-de][1,4-]benzoxazine-7,8-dione, 1-methylene-4-(4-methyl-1-piperazinyl)-5-fluoro-1,2,8,9-tetrahydro-7H-isoxazolo[4',5':5,6]pyrido[1,2,3-de][1,4]benzoxazine-7,8-dione, 1-methylene-4-(3-amino-1-pyrrolidinyl)-5-fluoro-1,2,8,9-tetrahydro-7H-isoxazolo[4',5':5,6]pyrido[1,2,3-de][1,4]benzoxazine-7,8-dione, 1-methylene-4-(3-methyl-1-piperazinyl)-5-fluoro-1,2,8,9-tetrahydro-7H-isoxazolo[4',5':5,6]pyrido[1,2,3-de][1,4]benzoxazine-7,8-dione and 1-methylene-4-(3-amino-4-methyl-1-pyrrolidinyl)-5-fluoro-1,2,8,9-tetrahydro-7H-isoxazolo[4',5'5,6]pyrido[1,2,3-de][1,4]benzoxazine-7,8-dione and 1-methyl-4-(4-amino methylphenyl)-5-fluoro-1,2,8,9-tetrahydro-7H-isoxazolo[4'5':5,6]pyrido[1,2,3-de][1,4]benzoxazine-7-8-dione.

Representative of such preferred compounds wherein B is sulfur are 1-methyl-4-(1-piperazinyl)-5-fluoro-1,2,8,9-tetrahydro-7H-isothiazolo[4',5':5,6-]pyrido[1,2,3-de][1,4]benzoxazine-7,8-dione, 1-methyl-4-(4-methyl-1-piperazinyl)-5-fluoro-1,2,8,9-tetrahydro-7H-isothiazolo[4',5':5,6]pyrido[1,2,3-de][1,4]benzoxazine-7,8-dione, 1-methyl-4-(3-amino-1-pyrrolidinyl)-5-fluoro-1,2,8,9-tetrahydro-7H-isothiazolo[4',5':5,6-]pyrido[1,2,3-de][1,4]benzoxazine-7,8-dione, 1-methyl-4-(3-methyl-1-piperazinyl)-5-fluoro-1,2,8,9-tetrahydro-7H-isothiazolo[4',5':5,6]pyrido[1,2,3-de][1,4]benzoxazine-7,8-dione, 1-methyl-4-(3-amino-4-methyl-1-pyrrolidinyl)-5-fluoro-1,2,8,9-tetrahydro-7H-isothiazolo[4',5':5,6]pyrido[1,2,3-de][1,4]benzoxazine-7,8-dione, 1-methyl-4-(2-methyl-1-piperazinyl-5-fluoro-1,2,8,9-tetrahydro-7H-isothiazolo[4',5':5,6]pyrido[1,2,3-de][1,4]benzoxazine-7,8-dione, 1-methyl-4-(-3-methyl-3-aminopyrrolidin-1-yl)-5-fluoro-1,2,8,9-tetrahydro-7H-isothiazolo[4',5':5,6]pyrido[1,2,3-de][1,4]benzoxazine-7,8-dione, 1-methyl-4-(2-methyl-4-amino pyrrolidin-1-yl)-5-fluoro-1,2,8,9-tetrahydro-7H-isothiazolo[4',5':5,6-]pyrido[1,2,3-de][1,4]benzoxazine-7,8-dione, 1-methyl-4-(2-(2,5-diazabicyclo[2.2.1]heptyl-5-fluoro-1,2,8,9-tetrahydro-7H-isothiazolo[4',5':5,6]pyrido[1,2,3-de][1,4-]benzoxazine-7,8-dione, 1-methyl-4-(3-N-ethylaminomethyl-pyrrolidin-1-yl)5-fluoro-1,2,8,9-tetrahydro-7H-isothiazolo-[4'5':5,6]pyrido[1,2,3-de][1,4-]benzoxazine-7,8-dione, 1-methylene-4- (4-methyl-1-piperazinyl)-5-fluoro-1,2,8,9-tetrahydro-7H-isothiazolo[4',5':5,6]pyrido[1,2,3-de][1,4]benzoxazine-7,8-dione, 1-methylene-4-(3-amino-1-pyrrolidinyl)-5-fluoro-1,2,8,9-tetrahydro-7H-isothiazolo[4',5':5,6]pyrido[1,2,3-de][1,4]benzoxazine-7,8-dione, 1-methylene-4-(3-methyl-1-piperazinyl-5-fluoro-1,2,8,9-tetrahydro-7H-isothiazolo[4',5':5,6]pyrido[1,2,3-de][1,4]benzoxazine-7,8-dione and 1-methylene-4-(3-amino-4-methyl-1-pyrrolidinyl)-5-fluoro-1,2,8,9-tetrahydro-7H-isothiazolo[4',5':5,6]pyrido[1,2,3-de][1,4]benzoxazine-7,8-dione.

Also included within the scope of the present invention are pharmaceutically acceptable salts of the foregoing compounds. As used herein, the term "pharmaceutically acceptable salts" refers to non-toxic acid addition salts and alkaline earth metal salts of the compounds of the invention. The salts can be prepared in situ during the final isolation and purification of the compounds of the invention, or separately by reacting the free base or acid functions with a suitable organic acid or base. Representative acid addition salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate glucoheptonate, lactobionate, lauryl sulfate salts and the like. Representative alkali or alkaline earth metal salts include the sodium, calcium, potassium and magnesium salts, etc. It has been found that the compounds of the present invention possess antibacterial activity against a wide spectrum of gram positive and gram negative bacteria, as well as enterobacteria. The compounds of the invention are, therefore, useful in the antibiotic treatment of susceptible bacterial infections in both humans and animals. In addition, the compounds, by reason of their in vitro activity, may be used in scrub solutions for surface inhibition of bacterial growth.

Susceptible organisms generally include those gram positive and gram negative, aerobic and anaerobic organisms whose growth can be inhibited by the compounds of the invention such as Staphylococcus, Lactobacillus, Streptococcus, Sarcina, Escherichia, Enterobacter, Klebseilla, Pseudomonas, Acinetobacter, Proteus, Citrobacter, Nisseria, Baccillus, Bacteroides, Peptococcus, Clostridium, Salmonella, Shigella, Serratia, Haemophilus, Brucella, and other organisms.

The compounds of the invention may also be formulated into compositions together with pharmaceutically acceptable carriers for parenteral injection, for oral administration in solid or liquid form, for rectal administration, and the like.

Compositions according to the invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying, and dispersing agents. They may be sterilized, for example, by filtration through a bacteria-retaining filter, or by incorporating sterilizing agents into the compositions. They can also be manufactured in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixers containing inert diluents commonly used in the art, such as water. Besides such inert diluents, compositions can also include adjuvants, such as wetting agents, emulsifying and suspending agents, and sweetening, flavoring and perfuming agents.

Compositions for rectal administration are preferably suppositories which may contain, in addition to the active substance, excipients such as cocoa butter or a suppository wax.

Actual dosage levels of active ingredient in the compositions of the invention may be varied so as to obtain an amount of active ingredient effective to achieve antibacterial activity in accordance with the desired method of administration. The selected dosage level, therefore, depends upon the nature of the active compound administered, the route of administration, the desired duration of treatment and other factors. Generally, daily dosage levels of the compounds of the invention of about 0.1 to about 750, more preferably about 0.25 to about 500 and most preferably about 0.5 to about 300 mg. of active ingredient per kg. of body weight are effective when administered orally to a mammalian patient suffering from an infection caused by a susceptible organism. If desired, the daily dose may be divided into multiple doses for administration, e.g., two to four time per day.

Compounds according to this invention wherin B is oxygen can be prepared by the following reaction scheme in which Z and R are as described above; $R_9$ is $C_1$ to $C_4$ alkyl group and $R_8$ is $C_1$ to $C_4$ alkyl or lower haloalkyl group such as chloromethyl, X is halogen such as a fluorine or chlorine atom and $R_{10}$ is $C_1$ to $C_4$ alkyl or a phenyl or substituted phenyl group.

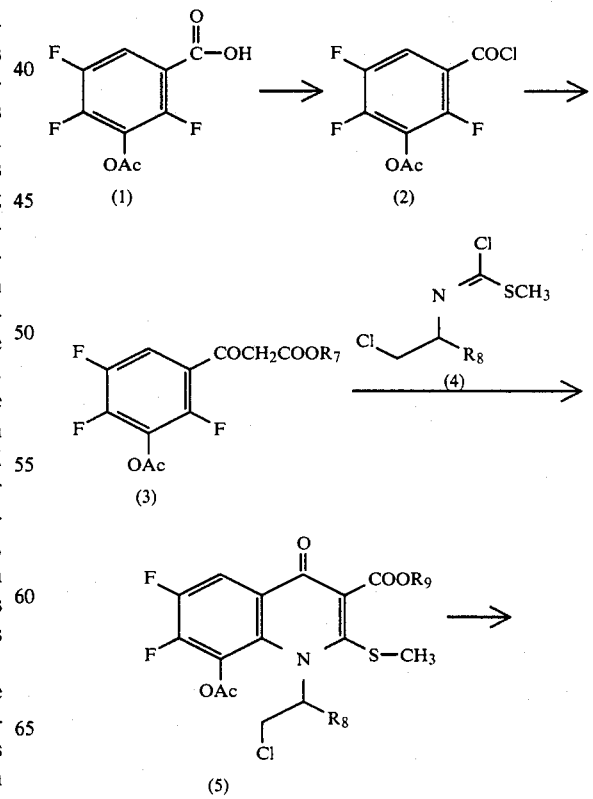

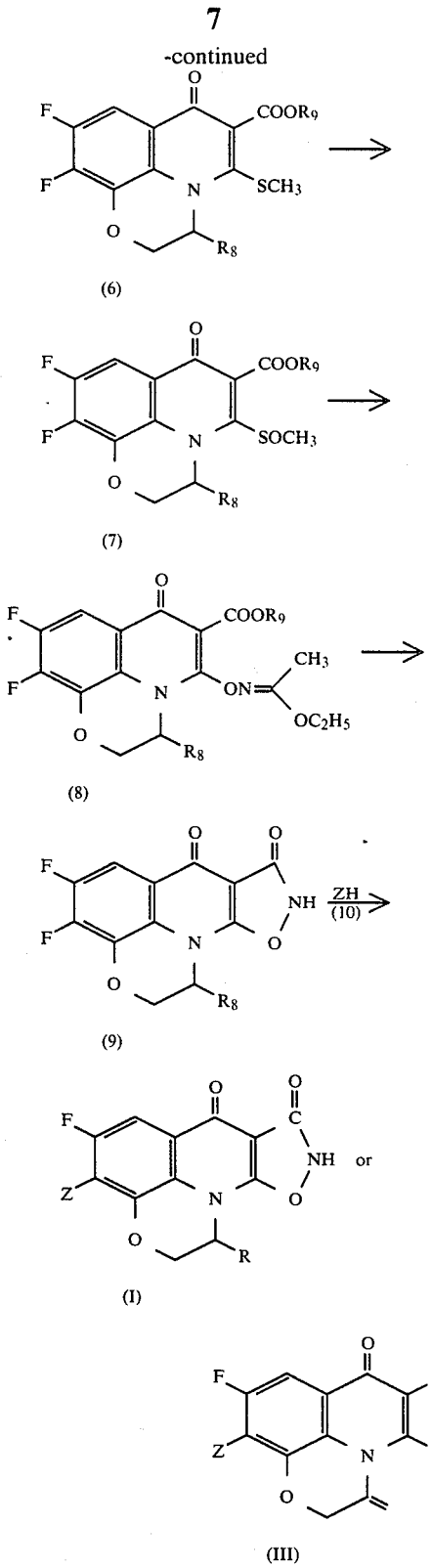

tetrahydrofuran with methyl N-substituted iminochlorothioformate (4) at room temperature or suitable elevated temperature as desired yields the 1,4-dihydro-4-oxo-quinoline-3-carboxylic acid ester (5).

Treatment of this ester (5) with dilute acid in aqueous acetonitrile for a period of time gives a phenol which is then reacted with sodium hydride to give the 9,10-difluoro-3-alkyl-5-methylthio-7-oxo-2,3-dihydro-7H-pyrido[1,2,3-de][1,4]benzoxazine-6-carboxylic acid ester (6).

Oxidation of this 6-carboxylic acid ester (6) with metachloroperbenzoic acid yields the sulfoxide (7). The reaction may be conducted at room temperature or elevated temperature in the presence of non-polar solvent such as methylene chloride or chloroform.

Reaction of the sulfoxide (7) with ethyl acetohydroxamate in the presence of a strong base such as sodium hydride or potassium t-butoxide in aprotic or non-aprotic solvent such as tetrahydrofuran at a temperature from 0° C. to elevated temperature yields the hydroxamate (8).

Treatment of the hydroxamate (8) with trifluoroacetic acid or dilute hydrochloric acid at room temperature or with perchloric acid at 0° C. for a short time yields the free hydroxylamine derivative which is then reacted with sodium bicarbonate in aqueous tetrahydrofuran at room temperature or suitable elevated temperature to yield the 1-alkyl (or haloalkyl)-4,5-difluoro-1,2,8,9-tetrahydro-7H-isoxazolo[4′,5′:5,6]pyrido[1,2,3-de][1,4-]benzoxazine-7,8-dione derivative (9).

Displacement of the 4-halogen of (9) with an amine (10) yields the 4-substituted amino-isoxazolo-pyridobenzoxazine (I). The reaction may be conducted at a temperature from 20° C. to 130° C. in the presence of a suitable organic polar or non-polar solvent such as pyridine, methylene chloride, chloroform, tetra-hydrofuran, 1-methyl-2-pyrrolidinone, dimethyl formamide or dimethyl-sulfoxide. It is desirable to carry out the reaction in the presence of an acid-acceptor such as triethylamine, potassium carbonate and the like at a molar ratio of 1.0 to 1.2 moles of the acid-acceptor per mole of the compound of the formula (9). The amine (10) can also be used as acid acceptor in which 2 or more molar excess of this reagent is used.

When Z is a phenyl or substituted phenyl (i.e., 10-fluoro in structure (7) is replaced by a phenyl or substituted phenyl group), the comound (7) is formed by coupling the compound (6) with a arylmetallic compound (i.e. phenyl lithium or substituted phenyl lithium) at the 10 position to displace the 10-fluoro with a phenyl or substituted group. The coupling reaction is carried out in a reaction-inert solvent, i.e., a solvent which does not interfere with the coupling reaction of the arylmetallic compound with the 10-halo-substituted compound (6). In this case, compounds 7, 8, and 9, are represented by a formula wherein the 10-fluoro will be a 10-phenyl or substituted phenyl group. Suitable reaction-inert solvents are ethers, e.g. diethylether, dimethoxyethane and tetrahydrofuran. Co-solvents may be used with ethers if desired. These co-solvents may be benzene, In accordance with the foregoing reaction scheme, the substituted benzoic acid (1) can be converted to its acid chloride (2) by treatment with thionyl chloride. Displacement of the acid chloride (2) with malonic acid half ester in the presence of n-butyl lithium yields the beta-ketoester (3). Treatment of the beta-keto ester (3) with sodium hydride in non-aprotic solvent, preferably toluene, tetramethylethylenediamine (TMEDA) and hexamethylphosphorictriamide (HMPA).

The arylmetallic compounds containing group Z may be prepared by known methods. For instance, they may be prepared by direct lithium-halogen exchange of the corresponding arylhalide using n-butyl, sec-butyl or t-butyl lithium followed by transmetallation by a wide variety of salts by known methods such as described by E. Negishi, Organometallica in Organic Synthesis, Vol. 1, page 104.

Alternatively, compounds according to this invention wherein B is oxygen can also be prepared by the following scheme.

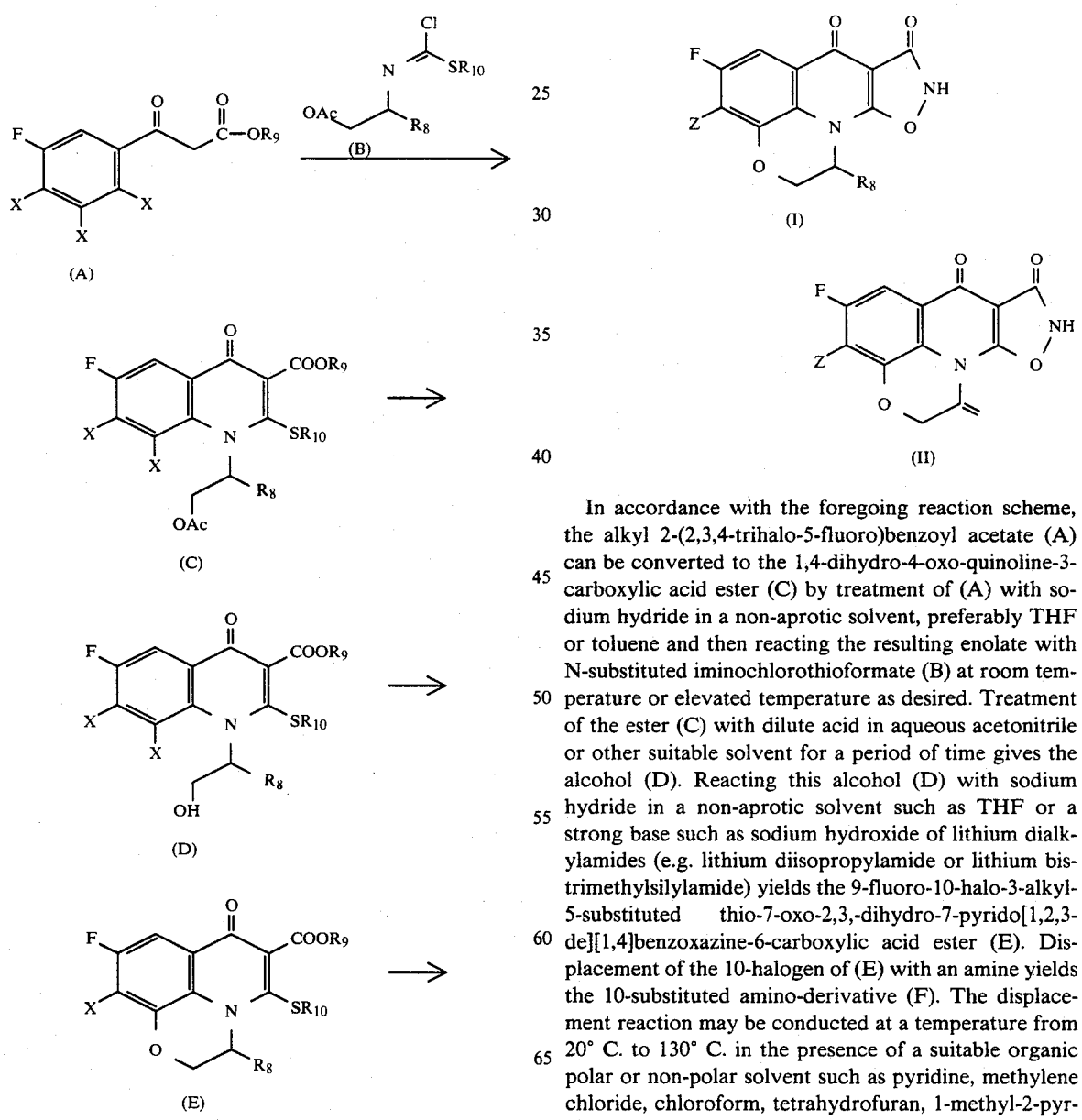

In accordance with the foregoing reaction scheme, the alkyl 2-(2,3,4-trihalo-5-fluoro)benzoyl acetate (A) can be converted to the 1,4-dihydro-4-oxo-quinoline-3-carboxylic acid ester (C) by treatment of (A) with sodium hydride in a non-aprotic solvent, preferably THF or toluene and then reacting the resulting enolate with N-substituted iminochlorothioformate (B) at room temperature or elevated temperature as desired. Treatment of the ester (C) with dilute acid in aqueous acetonitrile or other suitable solvent for a period of time gives the alcohol (D). Reacting this alcohol (D) with sodium hydride in a non-aprotic solvent such as THF or a strong base such as sodium hydroxide of lithium dialkylamides (e.g. lithium diisopropylamide or lithium bis-trimethylsilylamide) yields the 9-fluoro-10-halo-3-alkyl-5-substituted thio-7-oxo-2,3,-dihydro-7-pyrido[1,2,3-de][1,4]benzoxazine-6-carboxylic acid ester (E). Displacement of the 10-halogen of (E) with an amine yields the 10-substituted amino-derivative (F). The displacement reaction may be conducted at a temperature from 20° C. to 130° C. in the presence of a suitable organic polar or non-polar solvent such as pyridine, methylene chloride, chloroform, tetrahydrofuran, 1-methyl-2-pyrrolidinone, dimethylformamide or dimethylsulfoxide.

In case in structure (F) where the Z group is phenyl or substituted phenyl group, a coupling reaction is carried out from (E) in similar fashion as described in the preparation of (7) where the 10-fluoro is replaced with a phenyl or substituted phenyl group.

Oxidation of compound (F) with metachloroperbenzoic acid or other peracid in methylene chloride or other organic medium, or in a aqueous or non-aqueous acidic medium yields the sulfoxide (G). The reaction may be conducted at room temperature or elevated temperature. Treatment of the sulfoxide (G) with N-hydroxyurea in an aprotic or non-aprotic solvent such as ethanol, tertbutylalcohol, methanol, tetrahydrofuran, dimethylformamide, in the presence of a base such as 1,8-diazabicyclo[5.4.0]undec-7-ene (DBU), 1,5-diazobicyclo[4.3.0]non-5-ene (DBN), sodium hydride or potassium t-butoxide gives the 1-alkyl (or methylene)-4-substituted amino (or substituted phenyl)-5-fluoro-1,2,8,9-tetrahydro-7H-isoxazolo[4',5':5,6-]pyrido[1,2,3-de][1,4]benzoxazine-7,8-dione (I) or (II). The reaction may be conducted at room temperature or suitable elevated temperature.

Compounds according to this invention wherein B is sulfur can be prepared by the following reaction scheme in which Z and R are as described above; $R_7$ is $C_1$ to $C_4$ alkyl group and $R_8$ is $C_1$ to $C_4$ alkyl or lower haloalkyl group such as chloromethyl.

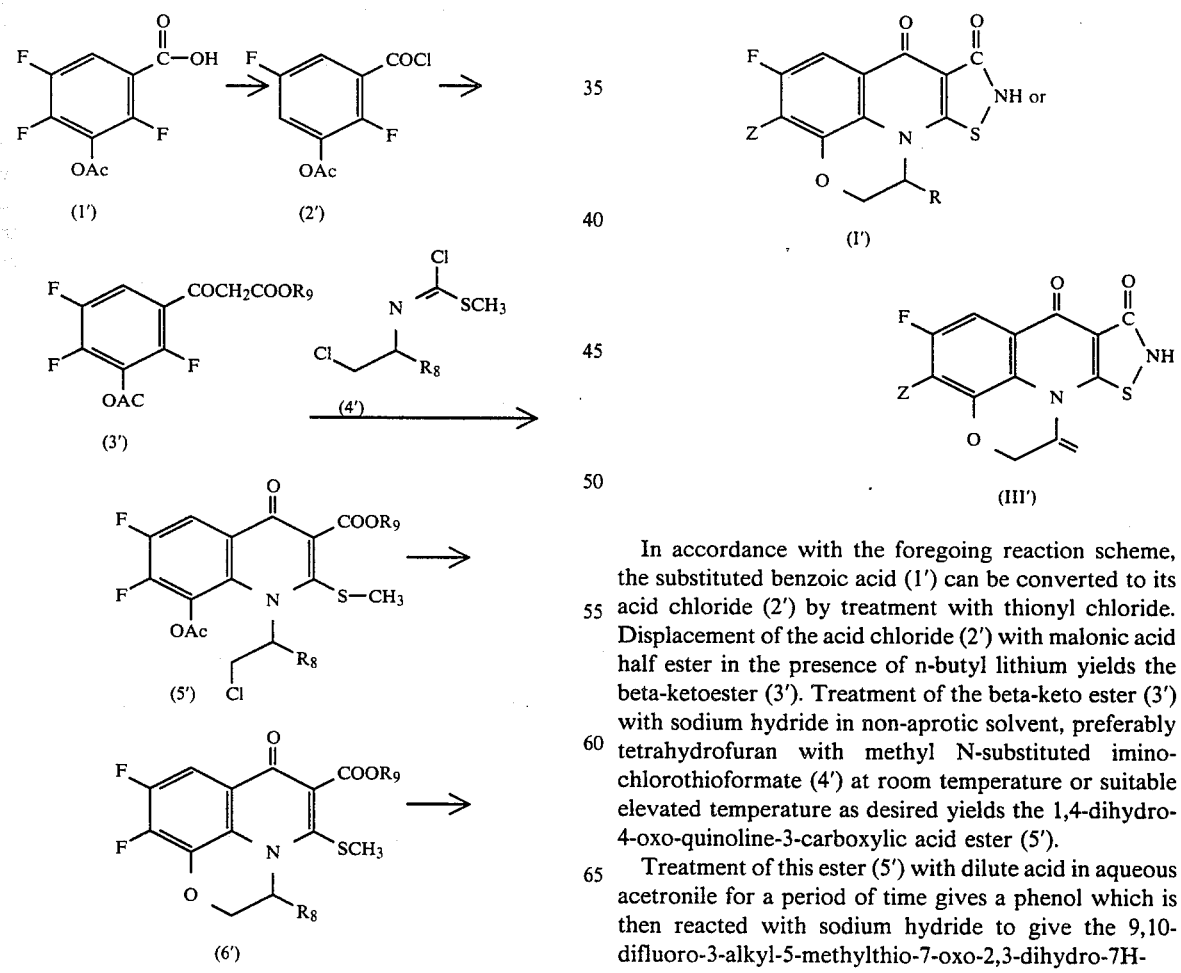

In accordance with the foregoing reaction scheme, the substituted benzoic acid (1') can be converted to its acid chloride (2') by treatment with thionyl chloride. Displacement of the acid chloride (2') with malonic acid half ester in the presence of n-butyl lithium yields the beta-ketoester (3'). Treatment of the beta-keto ester (3') with sodium hydride in non-aprotic solvent, preferably tetrahydrofuran with methyl N-substituted iminochlorothioformate (4') at room temperature or suitable elevated temperature as desired yields the 1,4-dihydro-4-oxo-quinoline-3-carboxylic acid ester (5').

Treatment of this ester (5') with dilute acid in aqueous acetronile for a period of time gives a phenol which is then reacted with sodium hydride to give the 9,10-difluoro-3-alkyl-5-methylthio-7-oxo-2,3-dihydro-7H- pyrido[1,2,3-de][1,4]benzoxazine-6-carboxylic acid ester (6).

Oxidation of this 6-carboxylic acid ester (6') with metachloroperbenzoic acid yields the sulfoxide (7'). The reaction may be conducted at room temperature or elevated temperature in the presence of non-polar solvent such as methylene chloride or chloroform.

Reaction of (7') with sodium hydrosulfide in an aprotic solvent, preferably aqueous tetrahydrofuran, at room or elevated temperature yields the 2-mercapto-derivative (8'). Treatment of (8') with hydroxylamine-O-sulfonic acid in the presence of a base, preferably sodium bicarbonate in aprotic solvent, preferably aqueous tetrahydrofuran yields the 1-alkyl (or haloalkyl)-4,5-difluoro-1,2,8,9-tetrahydro-7H-isothiazolo[4',5':5,6-]pyrido[1,2,3-de][1,4]benzoxazine-7,8-dione derivative (9').

Displacement of the 4-halogen of (9') with an amine (10') yields the 4-substituted amino-isothiazolo-pyrido-benzoxazine (I'). The reaction may be conducted at a temperature from 20° C. to 130° C. in the presence of a suitable organic polar or non-polar solvent such as pyridine, methylene chloride, chloroform, tetra-hydrofuran, 1-methyl-2-pyrrolidinone, dimethyl formamide or dimethyl-sulfoxide. It is desirable to carry out the reaction in the presence of an acid-acceptor such as triethylamine, potassium carbonate and the like at a molar ratio of 1.0 to 1.2 moles of the acid-acceptor per mole of the compound of the formula (9'). The amine (10') can also be used as acid acceptor in which 2 or more molar excess of this reagent is used.

When Z is a phenyl or substituted phenyl (i.e. the 10-fluoro group in structure (7') is replaced by a phenyl or substituted phenyl group) the compound (7') is formed by coupling the compound (6') with a arylmetallic compound (e.g. phenyl lithium or substituted phenyl lithium) at the 10 position to displace the 10-fluoro with a phenyl or subsituted group. The coupling reaction is carried out in a reaction-inert solvent, i.e., a solvent which does not interfere with the coupling reaction of the arylmetallic compound with the 10-halo-substituted compound (6'). In this case, compounds 7', 8', and 9' are represented by a formula wherein the 10-fluoro group will be a 10-phenyl or substituted phenyl group. Suitable reaction-inert solvents are ethers, e.g., dimethoxyethane, diethylehter and tetrahydrofuran. Co-solvents may be used with ethers if desired. These co-solvents may be benzene, toluene, tetramethylethylenediamine (TMEDA) and hexamethylphosphorictriamide (HMPA).

The arylmetallic compounds containing group Z may be prepared by known methods. For instance, they may be prepared by direct lithium-halogen exchange of the corresponding arylhalide using n-butyl, sec. butyl or t-butyl lithium followed by transmetallation by a wide variety of salts by known methods such as described by E. Negishi, Organometallics in Organic Synthesis, Vol. 1, page 104.

Alternatively, compounds according to this invention where B is sulfur can be prepared by the following scheme.

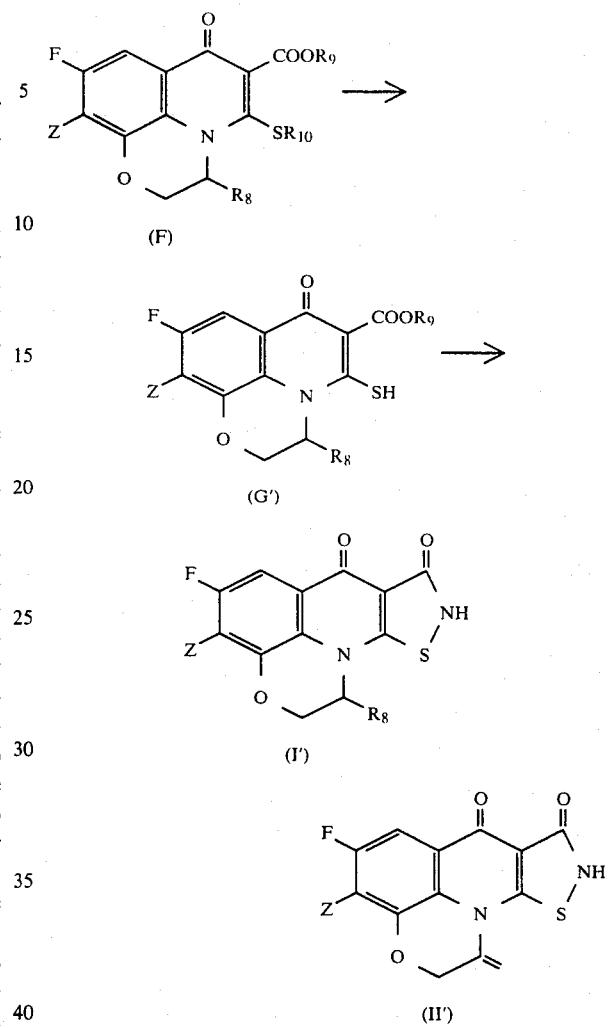

In accordance with the above scheme, treatment of the compound (F) with sodium hydrosulfide in an aprotic solvent, preferably aqueous tetrahydrofuran, at room temperature or elevated temperature yields the 2-mercapto derivative (G'). Reaction of compound (G') with hydroxylamine-O-sulfonic acid in the presence of a base, preferably sodium bicarbonate in aqueous tetrahydrofuran or other appropriate solvent yields the 1-alkyl (or methylene)-4-substituted amino or (substituted phenyl)-5-fluoro-1,2,8,9-tetrahydro-TH-isothiazolo[4',5':5,6]pyrido[1,2,3-de][1,4]benzoxazine-7,8'-dione derivative (I') or (II'). The reaction may be conducted at room temperature or suitable elevated temperature.

The foregoing may be better understood from the following examples, which are presented for purposes of illustration and are not intended to limit the scope of the inventive concepts. As used in the following examples, the references to compounds, such as (1), (2), (3) or (1'), (2'), (3'), etc., or (A), (B), (C) or (A'), (B'), (C"), and to substituents, such as R, R7, R8, Z, etc., refer to the corresponding compounds and substituents in the foregoing reaction scheme and in formulae I, III, I' and III'. Formulae I, III, I' and III' represent compounds according to structures previously described in this specification.

EXAMPLE 1

1-methyl-4-(4-methyl-1-piperazinyl)-5-fluoro-1,2,8,9-tetrahydro-7H-isoxazolo[4',5':5,6]pyrido[1,2,3-de][1,4-]benzoxazine-7,8-dione (a) A mixture of 1.17 g of 2,4,5-trifluoro-3-acetyloxybenzoic acid (1) and thionyl chloride (10 ml) and 1 drop of dimethylformamide is heated at refluxing temperature for 4 hours. The solution is evaporated to dryness to give the acid chloride (2). This acid chloride, dissolved in 10 ml of tetrahydrofuran (THF) is added slowly to a solution of 1.32 g of ethylmalonate monoester in 25 ml of THF solution containing 9.09 ml of 2.2 molar solution of n-butyl lithium in hexane at $-60°$ C. It is allowed to stir at $-55°$ C. to $-60°$ C. for 1 hour. The solution is allowed to warm up to room temperature and then acidified with 20 ml of 1N hydrochloric acid and extracted with ether. The ether extract is washed with saturated $NaHCO_3$ and then water, and dried to yield 1.29 g of the ketoester (3) ($R_9=C_2H_5$).

(b) 800 mg of a 60% sodium hydride-in-oil suspension is slowly added to a solution of 1.86 g methyl N-(2-chloro-1-methyl ethyl) iminochlorothioformate (4) ($R_8=CH_3$) and 4.34 g ketoester (3) ($R_9=C_2H_5$). The mixture is then heated at reflux for 24 hours. It is then cooled and evaporated under reduced pressure to dryness. The residue is dissolved in methylene chloride and washed with saturated sodium chloride solution. Organic layer is separated and dried over magnesium sulfate. The product is purified through silica gel column yielding the 1,4-dihydro-4-oxo-quinoline-3-carboxylate (5) ($R_9=C_2H_5$, $R_8=CH_3$).

(c) To a solution of 2.17 g of the preceding compound (5) ($R_9=C_2H_5$, $R_8=CH_3$) in 30 ml acetonitrile is added in 10 ml 2N hydrochloric acid solution. The mixture is stirred for 24 hours at room temperature. The mixture is then evaporated to dryness and redissolved in THF. 200 mg of sodium hydride is added. After heating for 24 hours at 50° C., the reaction mixture is then evaporated under reduced pressure to dryness. The residue is dissolved in methylene chloride and washed with water. The organic solvent is separated and dried and evaporated to dryness. After purification, it yields the 9,10-difluoro-3-methyl-5-methylthio-7-oxo-2,3-dihydro-7H-pyrido[1,2,3-de] [1,4]benzoxazine-6-carboxylic acid ethyl ester (6) ($R_9=C_2H_5$, $R_8=CH_3$).

(d) To a solution of 3.6 g of the preceding compound (6) ($R_9=C_2H_5$, $R_8=CH_3$) in 100 ml methylene chloride is added in 2.18 g of 80% metachloroperbenzoic acid. After stirring at 25° C. for 7 hours, the solution is diluted with 150 ml of methylene chloride and washed with dilute sodium bicarbonate solution. The organic solvent is dried over magnesium and evaporated to dryness. 15 ml of ether is added to the residue and it crystallized yielding, after filtration the sulfoxide (7) ($R_9=C_2H_5$, $R_8=CH_3$).

(e) 0.4 g of 60% sodium hydride in oil suspension is added slowly to a solution of 3.87 g of the preceding compound (7) ($R_9=C_2H_5$, $R_8=CH_3$) and 1.31 g of ethyl acetohydroxamate in 80 ml tetrahydrofuran. After stirring at room temperature for 24 hours, the mixture is evaporated to dryness and the residue is dissolved in methylene chloride (150 ml) and washed with water. The organic portion is dried and evaporated to dryness and the residue is purified by chromatography yielding the hydroxamate (8) ($R_9=C_2H_5$, $R_8=CH_3$).

(f) To a solution of 2.2 g of the preceding hydroxamate derivative (8) $R_9=C_2H_5$, $R_8=CH_3$) in 15 ml THF is added 70% perchloric acid (3 ml) with stirring at 0° C. for 10 minutes. The mixture is then poured into ice water yield a solid which is filtered. The solid is then dissolved in 60 ml water/THF mixture and 3.2 g sodium bicarbonate in 30 ml $H_2O$ is then added. After 5 hours, the mixture extracted with ether (25 ml×2). The aqueous layer is acidified with dilute hydrochloric acid to pH 3 and the precipitate is filtered yielding 1-methyl-4,5-difluoro-1,2,8,9-tetrahydro-7H-isoxazolo[4',5':5,6-]pyrido[1,2,3-de][1,4]benzoxazine-7,8-dione (9) ($R_8=CH_3$).

(g) To a solution of 1.45 g of the preceding isoxazolo-pyrido-benzoxazine derivative (9) ($R_8=CH_3$) in 30 ml pyridine is added in 2.5 ml N-methylpiperazine. It is then heated under nitrogen atmosphere at 50° C. for 24 hours. The mixture is evaporated to dryness and is then boiled in ethanol for 5 minutes and the mixture is filtered and washed with water yielding the 1-methyl-4-(4-methyl-1-piperazinyl)-5-fluoro-1,2,8,9-tetrahydro-7H-isoxazolo[4',5':5,6]pyrido[1,2,3-de][1,4]benzoxazine-7,8-dione (I)

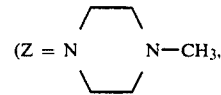

$R=CH_3$).

EXAMPLE 2

1-methyl-4-(1-piperazinyl)-5-fluoro-1,2,8,9-tetrahydro-7H-isoxazolo[4',5':5,6]pyrido[1,2,3-de][1,4]benzoxazine-7,8-dione (a) The procedure of Example 1 can be repeated, replacing the N-methylpiperazine in Example 1(g) with piperazine, to obtain 1-methyl-4-(1-piperazinyl)-5-fluoro-1,2,8,9-tetrahydro-7H-isoxazolo[4',5':5,6-]pyrido[1,2,3-de][1,4]benzoxazine-7,8-dione (I)

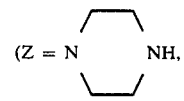

$R=CH_3$).

(b) Alternatively, the title compound is prepared as follows: To a solution of 2.64 g of ethyl 2,3,4,5-tetra-fluorobenzoylacetate (A) ($R_9=C_2H_5$, X=F) in 45 ml toluene at room temperature is added 0.41 g of a 60% sodium hydride-in-oil suspension. 2.72 g of the iminochlorothioformate (B) ($R_8=CH_3$, $R_{10}=C_6H_5$) is then added to the mixture. After ½ hours stirring, the mixture is heated at reflux for 18 hours. 1 ml of acetic acid is added to the mixture and the solvent is removed under reduced pressure. The residue is dissolved in methylene chloride (300 ml) and washed with saturated sodium chloride solution. The organic layer is dried and purified through silica gel column to give 2.5 g the 1,4-dihydro-4-oxoquinoline-3-carboxylate (C) ($R_8$=$CH_3$, $R_9$=$C_2H_5$, $R_{10}$=$C_6H_5$, X=F).

(c) 2 g of the preceding compound (C) is dissolved in 30 ml acetonitrile. 3 ml of 3N hydrochloric acid are added. The mixture is heated at 50° C. for 1 hour. The solvent is removed under reduced pressure. The residue is dissolved in 400 ml methylene chloride and washed with saturated sodium chloride solution. The organic layer is dried and purified to yield the alcohol (D). ($R_8$=$CH_3$, $R_9$=$C_2H_5$, $R_{10}$=$C_6H_5$, X=F).

(d) To a solution of 2.2 g of the preceding alcohol (D) ($R_8$=$CH_3$, $R_9$=$C_2H_5$, $R_{10}$=$C_6H_5$) in 30 ml THF at 0° C. is added 0.41 g of a 60% sodium hydride-in-oil suspension. The reaction is heated at 55° C. for 12 hours. Acetic acid (0.5 ml) is added and the solvent is removed under reduced pressure. The residue is dissolved in 500 ml methylene chloride and washed with saturated sodium chloride solution. The organic portion is dried and evaporated to dryness. Purification on silica gel column yields the benzoxazine (E) ($R_8$=$CH_3$, $R_9$=$C_2H_5$, $R_{10}$=$C_6H_5$, X=F)

(e) To a solution of 2.1 g of the benzoxazine (E) ($R_8$=$CH_3$, $R_9$=$C_2H_5$, $R_{10}$=$C_6H_5$, X=F), in 30 ml pyridine is added 8 g of N-carbobenzoxypiperazine. The mixture is heated at 70° C. for 18 hours. The solvent is removed by evaporation under reduced pressure. The residue is washed with ether, water and ether. It is dried, yielding 2.45 g of the carbobenzoxy-benzoxazine (F) ($R_8$=$CH_3$, $R_9$=$C_2H_5$, $R_{10}$=$C_6H_5$, Z=carbobenzoxy-piperazin-1-yl).

(f) To a solution of (F) ($R_8$=$CH_3$, $R_9$=$C_2H_5$, $R_{10}$=$C_6H_5$, Z=carbobenxozy-piperazin-1-yl) (3.06 g) in 200 ml methylene chloride at room temperature is added 1.06 g of m-chloro-perbenzoic acid. After 1 day, the solvent is diluted with 300 ml methylene chloride. The solution is washed with cold saturated sodium bicarbonate solution. The organic layer is dried and evaporated to dryness. Crystallizaion from ethanol yields the sulfoxide (G), ($R_8$=$CH_3$, $R_9$=$C_2H_5$, $R_{10}$=$C_6H_5$,

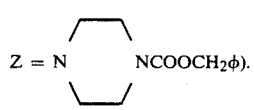

(g) To a solution of 3.2 g of the sulfoxide (G) ($R_8$=$CH_3$, $R_9$=$CH_2H_5$, $R_{10}$=$C_6H_5$,

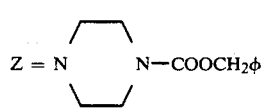

in 150 ml methanol is added in 385 hydroxyurea and 775 mg DBU (1,8-diazabicyclo[5.4.0]undec-7-ene). After 1 day, the solution is removed and 1 ml of acetic acid is added and water (300 ml) is added and filtered, yielding compound I

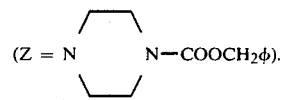

(h) 1 g of the preceding compound is dissolved in 5 ml of hydrogen bromide in glacial acetic acid. After 5 minutes, ether (150 ml) is added and filtered, and the residue washed with more ether to give the title compound as the hydrobromide salt in good yield.

EXAMPLE 3

1-methyl-4-(3-formamido-1-pyrrolidinyl)-5-fluoro-1,2,8,9-tetrahydro-7H-isoxazolo[4',5':5,6]pyrido[1,2,3-de][1,4]benzoxazine-7,8-dione (a) In the described fashion as Example 2(b)–2(e), replacing the N-carbobenzoxypiperazine in Example 2(e) with 3-formamidopyrrolidine, one can obtain compound (F) ($R_8$=$CH_3$, $R_9$=$C_2H_5$, $R_{10}$=$C_6H_5$,

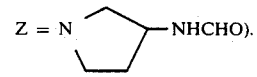

(b) Following the procedure as Example 2(f)–2(g), one can obtain 1-methyl-4-(3-formamido-1-pyrrolidinyl)-5-fluoro-1,2,8,9-tetrahydro-7H-isoxazolo[4',5':5,6]pyrido[1,2,3-de][1,4]benzoxazine-7,8-dione (I)

R=$CH_3$).

EXAMPLE 4

1-methyl-4-(3-amino-1-pyrrolidinyl)-5-fluoro-1,2,8,9-tetrahydro-7H-isoxazolo[4',5':5,6]pyrido[1,2,3-de][1,4-]benzoxazine-7,8-dione The product of Example 3, I

R=$CH_3$) can be hydrolyzed by the use of dilute hydrochloric acid in acetonitrile to yield 1-methyl-4-(3-amino-1-pyrrolidinyl)-5-fluoro-1,2,8,9-tetrahydro-7H-isoxazolo[4',5':5,6]pyrido[1,2,3-de][1,4]benzoxazine-7,8-dione hydrochloride salt (I)

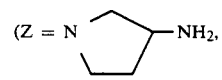

EXAMPLE 5

1-methyl-4-(3-amino-4-methyl-1-pyrrolidinyl)-5-fluoro-1,2,8,9-tetrahydro-7H-isoxazolo[4',5':5,6]pyrido[1,2,3-de][1,4]benzoxazine-7,8-dione The procedure of Example 1 can be repeated, replacing the N-methylpiperazine in Example 1(g) with 3-amino-4-methylpyrrolidine to obtain 1-methyl-4-(3-amino-4-methyl-1-pyrrolidinyl)-5-fluoro-1,2,8,9-tetrahydro-7H-isoxazolo[4',5':5,6]pyrido[1,2,3-de][1,4-]benzoxazine-7,8-dione (I)

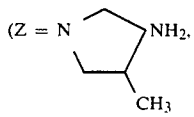

R=CH₃).

EXAMPLE 6

1-methyl-4-(3-methyl-1-piperazinyl)-5-fluoro-1,2,8,9-tetrahydro-7H-isoxazolo[4',5':5,6]pyrido[1,2,3-de][1,4-]benzoxazine-7,8-dione (a) In the described fashion as Example 2(b)–2(e), replacing the N-carbobenzoxypiperazine in Example 2(e) with 3-methyl-4-carbobenzoxypiperazine, one can obtain compound (F) ($R_8=CH_3$, $R_9=C_2H_5$, $R_{10}=C_6H_5$,

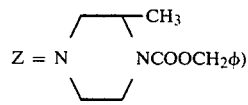

(b) Following the procedure described in Example 2(f)–2(h), one can obtained 1-methyl-4-(3-methyl-1-piperazinyl)-5-fluoro-1,2,8,9-tetrahydro-7H-isoxazolo[4',5':5,6]pyrido[1,2,3-de][1,4]benzoxazine-7,8-dione (I)

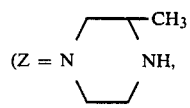

R=CH₃)hydromide salt.

EXAMPLE 7

1-methyl-4-(3-methyl-3-aminopyrrolidin-1yl)-5-fluoro-1,2,8,9,-tetrahydro-7H-isoxazolo[4',5':5,6]pyrido[1,2,3-de][1,4]benzoxazine-7,8-dione (a) The procedure of Example 2(b)–2(e) can be repeated, replacing the N-methylpiperazine in Example 2(e) with 3-methyl-3-carbobenzoxyamino-1-pyrrolindine to obtain compound (F) ($R_8=CH_3$, $R_9=C_2H_5$, $R_{10}=C_6H_5$,

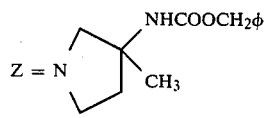

(b) Following the procedure described in Example 2(f)–2(h), one can obtain 1-methyl-4-(3-methyl-3-aminopyrrolidin-1-yl)-5-fluoro-1,2,8,9-tetrahydro-7H-isoxazolo [4'5':5,6]pyrido[1,2,3-de][1,4]benzoxazine-7,8-dione (I)

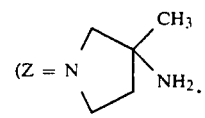

EXAMPLE 8

1-methyl-4-(1-thiomorpholinyl)-5-fluoro-1,2,8,9-tetrahydro-7H-isoxazolo[4',5':5,6]pyrido[1,2,3-de][1,4]benzoxazine-7,8-dione In the described fashion as Example 1, replacing the N-methylpiperazine in Example 1(g) with thiomorpholine, one can obtain 1-methyl-4-(1-thiomorpholinyl)-5-fluoro-1,2,8,9-tetrahydro-7H-isoxazolo[4',5':5,6-]pyrido[1,2,3-de][1,4]benzoxazine-7,8-dione (I)

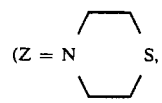

R=CH₃).

EXAMPLE 9

1-methyl-4-(3-N-ethylaminomethylpyrrodin-1-yl)-5-fluoro-1,2,8,9-tetrahydro-7H-isoxazolo[4',5':5,6-]pyrido[1,2,3-de][1,4]benzoxazine-7,8-dione (a) The procedure of Example 2(b)–2(e) can be repeated, replacing the N-carbobenzoxypiperazine in Example 2(e) with 3(N-carbobenzoxy N-ethyl)aminomethyl-1-pyrrolidine, to obtain the Compound (F) ($R_8=CH_3$, $R_9=C_2H_5$, $R_{10}=C_6H_5$,

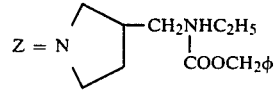

(b) Following the procedure described in Example 2(f)–2(h), one can obtain 1-methyl-4-(3-N-ethylamino methylpyrrolidin-1-yl)-5-fluoro-1,2,8,9-tetrahydro-7H-isoxazolo[4',5':5,6]pyrido[1,2,3-de][1,4]benzoxazine-7,8-dione (I)

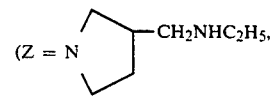

R=CH₃).

EXAMPLE 10

1-methyl-4-(3-aminomethyl-1-pyrrolidinyl)-5-fluoro-1,2,8,9-tetrahydro-7H-isoxazolo[4',5':5,6]pyrido[1,2,3-de][1,4]benzoxazine-7,8-dione (a) The procedure of Example 2(b)–2(e) can be repeated, replacing the N-carbobenzoxypiperazinyl in Example 2(e) with 3-N-carbobenzoxy aminomethyl-1-pyrrolidine, to obtain compound (F) ($R_8=CH_3$, $R_9=C_2H_5$, $R_{10}=C_6H_5$,

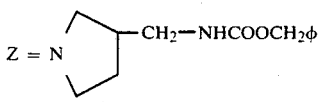

(b) Following the procedure described in Example 2(f)–2(h), one can obtain 1-methyl-4-(3-aminomethyl-1-pyrrolidinyl)-5-fluoro-1,2,8,9-tetrahydro-7H-isoxazolo[4',5':5,6]pyrido[1,2,3-de][1,4]benzoxazine-7,8-dione (I)

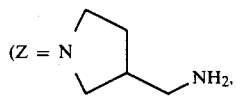

$R=CH_3$).

EXAMPLE 11

In the described fashion as in Example 1, replacing N-methylpiperazine in 1(g) with an appropriate amine such as ethyl amine, ethanolamine, 1,2-diaminoethane, N-methylhydrazine, 3-hydroxymethyl-1-pyrrolidine, 3-methylaminopyrrolidine, 2-p-fluorophenylpiperazine, 3-hydroxypyrrolidine, 3-aminomethyl-4-chloropyrrolidine, one can obtain the following compounds.

(a) 1-methyl-4-ethylamino-5-fluoro-1,2,8,9-tetrahydro-7H-isoxazolo[4',5':5,6]pyrido[1,2,3-de][1,4]benzoxazine-7,8-dione (I) ($Z=NHC_2H_5$ $R=CH_3$).

(b) 1-methyl-4-aminoethylamino-5-fluoro-1,2,8,9-tetrahydro-7H-isoxazolo[4',5':5,6]pyrido[1,2,3-de][1,4]benzoxazine-7,8-dione (I) ($Z=NHC_2H_4NH_2$, $R=CH_3$).

(c) 1-methyl-4-hydroxyethylamino-5-fluoro-1,2,8,9-tetrahydro-7H-isoxazolo[4',5':5,6]pyrido[1,2,3-de][1,4]benzoxazine-7,8-dione (I) ($Z=NHC_2H_4-OH$, $R=CH_3$).

(d) 1-methyl-4(2-methyl-1-hydrazyl)-5-fluoro-1,2,8,9-tetrahydro-7H-isoxazolo[4',5':5,6]pyrido[1,2,3-de][1,4]benzoxazine-7,8-dione (I) $Z=(NHNHCH_3$, $R=CH_3)$, (e) 1-methyl-4-(3-hydroxymethyl-1-pyrrolidinyl)-5-fluoro-1,2,8,9-tetrahydro-7H-isoxazolo[4',5':5.6]pyrido[1,2,3-de][1,4]benzoxazine-7,8-dione (I)

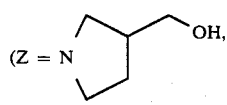

$R=CH_3$).

(f) 1-methyl-4-(3-methylamino-1-pyrrolidinyl)-5-fluoro-1,2,8,9-tetrahydro-7H-isoxazolo[4',5':5,6-]pyrido[1,2,3-de][1,4]benzoxazine-7,8-dione (I)

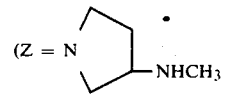

$R=CH_3$).

(g) 1-methyl-4-(3-p-fluorophenyl-1-piperazinyl)-5-fluoro-1,2,8,9-tetrahydro-7H-isoxazolo[4',5':5,6-]pyrido[1,2,3-de][1,4]benzoxazine-7,8-dione (I)

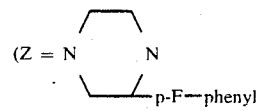

(h) 1-methyl-4-(3-hydroxy-1-pyrrolidinyl)-5-fluoro-1,2,8,9-tetrahydro-7H-isoxazolo[4',5':5,6]pyrido[1,2,3-de][1,4]benzoxazine-7,8-dione (I)

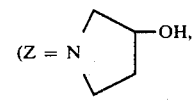

$R=CH_3$).

(i) 1-methyl-4-(3-aminomethyl-4-chloro-1-pyrrolidinyl)-5-fluoro-1,2,8,9-tetrahydro-7H-isoxazolo[4',5':5,6]pyrido[1,2,3-de][1,4]benzoxazine-7,8-dione (I)

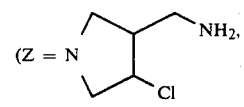

$R=CH_3$).

EXAMPLE 12

1-methylene-4-(1-methylpiperazinyl)-5-fluoro-1,2,8,9-tetrahydro-7H-isoxazolo[4',5':5,6]pyrido[1,2,3-de][1,4]benzoxazine-7,8-dione (a) In the described fashion in Example 1(b) replacing methyl N-(2-chloro-1-methylethyl) iminochlorothioformate (4) ($R_8=CH_3$) with methyl N-(2-chloro-1-chloromethylethyl)iminochlorothioformate (4) $R_8=CH_2Cl$) one can obtain the 1,4-dihydro-4-oxoquinoline-3-carboxylate (5) ($R_9=C_2H_5$, $R_8=CH_2Cl$).

(b) By following Example 1 (c–f), the preceding compound (5) ($R_9=C_2H_5$, $R_8=CH_2Cl$) can yield 1-chloromethyl-4,5-difluoro-1,2,8,9-tetrahydro-7H-isoxazolo[4',5':5,6]pyrido[1,2,3-de][1,4]benzoxazine-7,8-dione (9) ($R_8CH_2Cl$).

(c) In the described fashion as Example 1(g) displacing the 4-fluoro with N-methylpiperazine, the preceding compound (9) can yield 1-methylene-4-(4-methyl-1-piperazinyl)-5-fluoro-1,2,8,9-tetrahydro-7H-isoxazolo[4',5':5,6]pyrido[1,2,3-de][1,4]benzoxazine-7,8-dione (III).

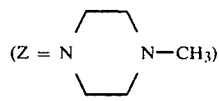
(Z = N⟨⟩N—CH₃)

EXAMPLE 13

By following the example 12(a–c), replacing the N-methylpiperazine in 12(c) with various amines such as piperazine, 3-formamidopyrrolidine, piperidine, pyrrolidine, morpholine, thiomorpholine, homopiperazine, N-N-dimethylhydrazine, 2-methylpiperazine, 2-phenylpiperazine, 3-amino-4-methylpyrrolidine one can obtain the following compounds.

(a) 1-methylene-4-(1-piperazinyl)-5-fluoro-1,2,8,9-tetrahydro-7H-isoxazolo[4′,5′:5,6]pyrido[1,2,3-de][1,4-]benzoxazine-7,8-dione (III)

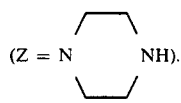
(Z = N⟨⟩NH).

(b) 1-methylene-4-(3-formamido-1-pyrrolidinyl)-5-fluoro-1,2,8,9-tetrahydro-7H-isoxazolo[4′,5′:5,6-]pyrido[1,2,3-de][1,4]benzoxazine-7,8-dione (III)

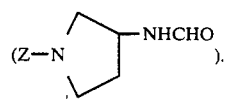
(Z—N⟨⟩—NHCHO).

(c) 1-methylene-4-(1-piperidinyl)-5-fluoro-1,2,8,9-tetrahydro-7H-isoxazolo[4′,5′:5,6]pyrido[1,2,3-de][1,4-]benzoxazine-7,8-dione (III)

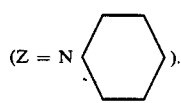
(Z = N⟨⟩).

(d) 1-methylene-4-(1-pyrrolidinyl)-5-fluoro-1,2,8,9-tetrahydro-7H-isoxazolo[4′,5′:5,6]pyrido[1,2,3-de][1,4-]benzoxazine-7,8-dione (III)

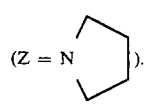
(Z = N⟨⟩).

(e) 1-methylene-4-(1-morpholinyl)-5-fluoro-1,2,8,9-tetrahydro-7H-isoxazolo[4′,5′:5,6]pyrido[1,2,3-de][1,4-]benzoxazine-7,8-dione (III)

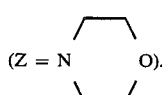
(Z = N⟨⟩O).

(f) 1-methylene-4-(1-thiomorpholinyl)-5-fluoro-1,2,8,9-tetrahydro-7H-isoxazolo[4′,5′:5,6]pyrido[1,2,3-de][1,4]benzoxazine-7,8-dione (III)

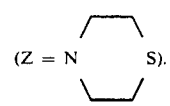
(Z = N⟨⟩S).

(g) 1-methylene-4-(1-homopiperazinyl)-5-fluoro-1,2,8,9-tetrahydro-7H-isoxazolo[4′,5′:5,6]pyrido[1,2,3-de][1,4]benzoxazine-7,8-dione (III)

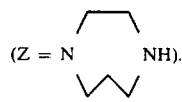
(Z = N⟨⟩NH).

(h) 1-methylene-4-(1-N,N-dimethylhydrazyl)-5-fluoro-1,2,8,9-tetrahydro-7H-isoxazolo[4′,5′:5,6-]pyrido[1,2,3-de][1,4]benzoxazine-7,8-dione (III) (Z=NHN(CH₃)₂).

(i) 1-methylene-4-(3-methyl-1-piperazinyl)-5-fluoro-1,2,8,9-tetrahydro-7H-isoxazolo[4′,5′:5,6]pyrido[1,2,3-de][1,4]benzoxazine-7,8-dione (III)

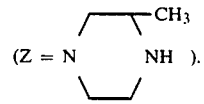
(Z = N⟨⟩NH) with CH₃.

(j) 1-methylene-4-(3-phenyl-1-piperazinyl)-5-fluoro-1,2,8,9-tetrahydro-7H-isoxazolo[4′,5′:5,6]pyrido [1,2,3-de][1,4]benzoxazine-7,8-dione (III)

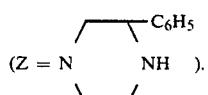
(Z = N⟨⟩NH) with C₆H₅.

(k) 1-methylene-4-(3-amino-4-methyl-1-pyrrolidinyl)-5-fluoro-1,2,8,9-tetrahydro-7H-isoxazolo[4′,5′:5,6-]pyrido[1,2,3-de][1,4]benzoxazine-7,8-dione (III)

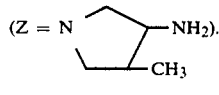
(Z = N⟨⟩—NH₂) with CH₃.

EXAMPLE 14

1-methylene-4-(3-amino-1-pyrrolidinyl)-5-fluoro-1,2,8,9-tetrahydro-7H-isoxazolo-[4′,5′:5,6]pyrido[1,2,3-de][1,4]benzoxazine-7,8-dione By following the procedure as Example (4), the product of Example 13(b) can be hydrolyzed to yield 1-methylene-4-(3-amino-1-pyrrolidinyl)-5-fluoro-1,2,8,9-tetrahydro-7H-isoxazolo[4′,5′:5,6]pyrido[1,2,3-de][1,4-]benzoxazine-7,8-dione hydrochloride salt (III)

(Z = N⟨⟩—NH₂).

EXAMPLE 15

1-methyl-4-(4-methyl-1-piperazinyl)-5-fluoro-1,2,8,9-tetrahydro-7H-isothiazolo[4',5':5,6]pyrido[1,2,3-de][1,4]benzoxazine-7,8-dione (a) A mixture of 1.17 g of 2,4,5-trifluoro-3-acetyloxybenzoic acid (1') and thionyl chloride (10 ml) and 1 drop of dimethylformamide is heated at refluxing temperature for 4 hours. The solution is evaporated to dryness to give the acid chloride (2'). This acid chloride, dissolved in 10 ml of tetrahydrofuran (THF) is added slowly to a solution of 1.32 g of ethylmalonate monoester in 25 ml of THF solution containing 9.09 ml of 2.2 molar solution of n-butyl lithium in hexane at $-60°$ C. It is allowed to stir at $-55°$ C. to $-60°$ C. for 1 hour. The solution is allowed to warm up to room temperature and then acidified with 20 ml of 1N hydrochloric acid and extracted with ether. The ether extract is washed with saturated $NaHCO_3$ and then water, and dried to yield 1.29 g of the ketoester (3') ($R_9=C_2H_5$).

(b) 800 mg of a 60% sodium hydride-in-oil suspension is slowly added to a solution of 1.86 g methyl N-(2-chloro-1-methyl ethyl)iminochlorothioformate (4) ($R_8=CH_3$) and 4.34 g ketoester (3') ($R_9=C_2H_5$). The mixture is then heated at reflux for 24 hours. It is then cooled and evaporated under reduced pressure to dryness. The residue is dissolved in methylene chloride and washed with saturated sodium chloride solution. Organic layer is separated and dried over magnesium sulfate. The product is purified through silica gel column yielding the 1,4-dihydro-4-oxo-quinoline-3-carboxylate (5') ($R_9=C_2H_5$, $R_8=CH_3$).

(c) To a solution of 2.17 g of the preceding compound (5') ($R_9=C_2H_5$, $R_8=CH_3$) in 30 ml acetonitrile is added in 10 ml 2N hydrochloric acid solution. The mixture is stirred for 24 hours at room temperature. The mixture is then evaporated to dryness and redissolved in THF. 200 mg of sodium hydride is added. After heating for 24 hours at 50° C., the reaction mixture is then evaporated under reduced pressure to dryness. The residue is dissolved in methylene chloride and washed with water. The organic solvent is separated and dried and evaporated to dryness. After purification, it yields the 9,10-difluoro-3-methyl-5-methylthio-7-oxo-2,3-dihydro-7H-pyrido[1,2,3-de][1,4]benzoxazine-6-carboxylic acid ethyl ester (6') ($R_9=C_2H_5$, $R_8=CH_3$).

(d) To a solution of 3.6 g of the preceding compound (6') ($R_7=C_2H_5$, $R_8=CH_3$) in 100 ml methylene chloride is added in 2.18 g of 80% metachloroperbenzoic acid. After stirring at 25° C. for 7 hours, the solution is diluted with 150 ml of methylene chloride and washed with dilute sodium bicarbonate solution. The organic solvent is dried over magnesium and evaporated to dryness. 15 ml of ether is added to the residue and it crystallized yielding, after filtration the sulfoxide (7') ($R_9=C_2H_5$, $R_8=CH_3$).

(e) 2.18 ml of 0.92N sodium hydrosulfide solution is added to 770 mg of the preceding sulfone (7') ($R_9=C_2H_5$, $R_8=CH_3$) in 10 ml THF. After the solution is stirred at room temperature, the solution is diluted with 30 ml water containing 252 mg $NaHCO_3$ and extracted with ether twice. The aqueous solution is cooled to 5° C. and acidified with 6 ml 1N hydrochloric acid. The precipitate is filtered and dried yielding the ethyl 9,10-difluoro-3-methyl-5-mercapto-7-oxo-2,3-dihydro-7H-pyrido[1,2,3-de][1,4]benzoxazine-6-carboxylate (8') ($R_9=C_2H_5$, $R_8=CH_3$).

(f) To a solution of 341 mg of the preceding compound (8') ($R_9=C_2H_5$, $R_8=CH_3$) in 8 ml of tetrahydrofuran and 20 ml of water solution containing 2.4 g sodium bicarbonate is added in 450 mg hydroxylamine—O—sulfonic acid. After stirring for 5 hours, the mixture is diluted with water (40 ml) and extracted with ether (25 ml×2). The aqueous layer is acidified to pH 3 and the precipitate is filtered yielding 1-methyl-4,5-difluoro-1,2,8,9-tetrahydro-7H-isothiazolo[4',5':5,6-]pyrido[1,2,3-de][1,4]benzoxazine-7,8-dione (9') ($R_8=CH_3$).

(g) To a solution of 1.5 g of the preceding isothiazolopyrido-benzoxazine derivative (9') ($R_8=CH_3$) in 30 ml pyridine is added in 2.5 ml N-methylpiperazine. It is then heated under nitrogen atmosphere at 50° C. for 24 hours. The mixture is evaporated to dryness and is then boiled in ethanol for 5 minutes and the mixture is filtered and washed with water yielding the 1-methyl-4-(4-methyl-1-piperazinyl)-5-fluoro-1,2,8,9-tetrahydro-7H-isothiazolo[4',5':5,6]pyrido[1,2,3-de][1,4]benzoxazine-7,8-dione (I')

$R=CH_3$).

EXAMPLE 16

1-methyl-4-(1-piperazinyl)-5-fluoro-1,2,8,9-tetrahydro-7H-isothiazolo[4',5':5,6]pyrido[1,2,3-de][1,4]benzoxazine-7,8-dione (a) The procedure of Example 15 can be repeated, replacing the N-methylpiperazine in Example 1(g) with piperazine, to obtain 1-methyl-4-(1-piperazinyl)-5-fluoro-1,2,8,9-tetrahydro-7H-isothiazolo[4',5':5,6-]pyrido[1,2,3-de][1,4]benzoxazine 7,8-dione (I')

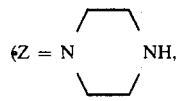

$R=CH_3$).

(b) Alternatively, the title compound is prepared as follows: To a solution of 3.2 g of (F) ($R_8=CH_3$, $R_9=C_2H_5$, $R_{10}=C_6H_5$,

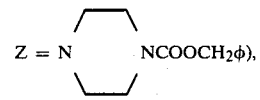

product of Example 2(e) in 40 ml THF is added 850 mg of sodium hydrosulfide in 2 ml of water. The mixture is stirred at room temperature for 10 hours. The solvent is removed by reduced pressure and the residue is dissolved in water (200 ml). Acetic acid is added until pH of the solution is 6. The precipitate is filtered and washed with water and then ether yielding (G') in good yield. ($R_8$=$CH_3$, $R_9$=$C_2H_5$,

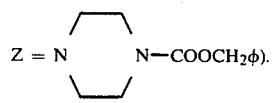

(c) To a solution of 1.2 g of (G') ($R_8$=$CH_3$, $R_9$=$C_2H_5$,

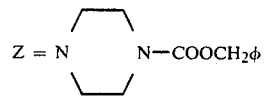

in 25 ml of THF and 15 ml water solution containing 1 g of sodium bicarbonate is added 850 mg hydroxylamine-O-sulfonic acid. After stirring for 1 day, the precipitate is filtered yielding (I')

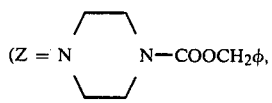

$R_8$=$CH_3$). The aqueous phrase is acidified with 0.1N Hydrochloric acid until pH is 7. Another crop of (I') is collected by filtration.

(d) 1 g of the preceding compound is dissolved in 5 ml hydrogen bromide in glacial acetic acid. After 5 minutes, ether (150 ml) is added and the residue is filtered and washed with ether yielding the title compound as the hydrobromide salt in good yield.

EXAMPLE 17

1-methyl-4-(3-formamido-1-pyrrolidinyl)-5-fluoro-1,2,8,9-tetrahydro-7H-isothiazolo[4',5':5,6]pyrido[1,2,3-de][1,4]benzoxazine-7,8-dione In the described fashion as Example 16(b)–16(c), replacing the compound (F) in Example 16(b) with compound (F) of Example 3(a) where $R_8$=$CH_3$, $R_9$=$C_2H_5$, $R_{10}$=$C_6H_5$,

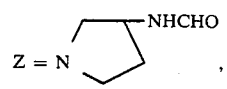

one can obtain 1-methyl-4-(3-formamido-1-pyrrolidinyl)-5-fluoro-1,2,8,9-tetrahydro-7H-isothiazolo[4',5':5,6]pyrido[1,2,3-de][1,4]benzoxazine-7,8-dione (I')

R=$CH_3$).

EXAMPLE 18

1-methyl-4-(3-amino-1-pyrrolidinyl)-5-fluoro-1,2,8,9-tetrahydro-7H-isothiazolo[4',5':5,6]pyrido[1,2,3-de][1,4]benzoxazine-7,8-dione The product of Example 17, I'

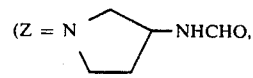

R=$CH_3$) can be hydrolyzed by the use of dilute hydrochloric acid in acetonitrile to yield 1-methyl-4-(3-amino-1-pyrrolidinyl)-5-fluoro-1,2,8,9-tetrahydro-7H-isothiazolo[4',5':5,6]pyrido[1,2,3-de][1,4]benzoxazine-7,8-dione hydrochloride salt (I')

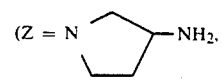

R=$CH_3$).

EXAMPLE 19

1-methyl-4-(3-amino-4-methyl-1-pyrrolidinyl)-5-fluoro-1,2,8,9-tetrahydro-7H-isothiazolo[4',5':5,6]pyrido[1,2,3-de][1,4]benzoxazine-7,8-dione The procedure of Example 16(b)–16(d) can be repeated, replacing the compound (F) in Example 16(b) with compound (F) of Example 6(a) where $R_8$=$CH_3$, $R_9$=$C_2H_5$, $R_{10}$=$C_6H_5$

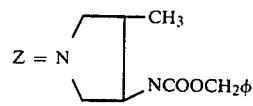

to obtain 1-methyl-4-(3-amino-4-methyl-1-pyrrolidinyl)-5-fluoro-1,2,8,9-tetrahydro-7H-isothiazolo[4',5':5,6-]pyrido[1,2,3-de][1,4]benzoxazine-7,8-dione ((')

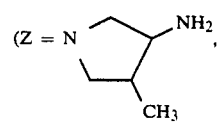

R=$CH_3$).

EXAMPLE 20

1-methyl-4-(1-piperidinyl)-5-fluoro-1,2,8,9-tetrahydro-7H-isothiazolo[4',5':5,6]pyrido[1,2,3-de][1,4]benzoxazine-7,8-dione In the described fashion as Example 15, replacing the N-methylpiperazine in Example 15(g) with piperidine, one can obtain 1-methyl-4-(1-piperidinyl)-5-fluoro-1,2,8,9-tetrahydro-7H-isothiazolo[4',5':5,6]pyrido[1,2,3-de][1,4]benzoxazine-7,8-dione (I')

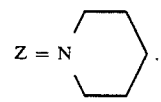

EXAMPLE 21

1-methyl-4-(3-methyl-3-aminopyrrolidin-1-yl)-5-fluoro-1,2,8,9-tetrahydro-7H-isothiazolo[4',5':5,6]pyrido[1,2,3-de][1,4]benzoxazine-7,8-dione The procedure of Example 16(b)–16(d) can be repeated, replacing the compound (F) in Example 16(b) with compound (F) of Example 7(a) where $R_8=CH_3$, $R_9=C_2H_3$, $R_{10}=C_6H_5$,

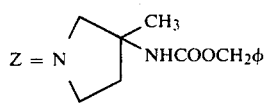

to obtain 1-methyl-4-(1-morpholinyl)-5-fluoro-1,2,8,9-tetrahydro-7H-isothiazolo[4',5':5,6]pyrido[1,2,3-de][1,4-]benzoxazine-7,8-dione (I')

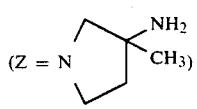

EXAMPLE 22

1-methyl-4-(1-thiomorpholinyl)-5-fluoro-1,2,8,9-tetrahydro-7H-isothiazolo[4',5':5,6]pyrido[1,2,3-de][1,4-]benzoxazine-7,8-dione In the described fashion as Example 15, replacing the N-methylpiperazine in Example 15(g) with thiomorpholine, one can obtain 1-methyl-4-(1-thiomorpholinyl)-5-fluoro-1,2,8,9-tetrahydro-7H-isothiazolo[4',5':5,6]pyrido[1,2,3-de][1,4]benzoxazine-7,8-dione (I')

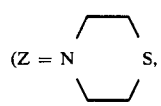

$R=CH_3$).

EXAMPLE 23

1-methyl-4-(3-N-ethylaminomethylpyrrolidin-1-yl)-5-fluoro-1,2,8,9-tetrahydro-7H-isothiazolo[4',5':5,6-]pyrido[1,2,3-de][1,4]benzoxazine-7,8-dione The procedure of Example 16(b)–16(d) can be repeated, replacing the compound (F) in Example 16(b) with compound (F) of Example 9(a) where $R_8=CH_3$, $R_9=C_2H_5$, $R_{10}=C_6H_5$,

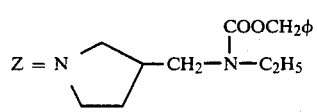

to obtain 1-methyl-4-(1-homopiperazinyl)-5-fluoro-1,2,8,9-tetrahydro-7H-isothiazolo[4',5':5,6]pyrido[1,2,3-de][1,4]benzoxazine-7,8-dione (I')

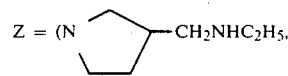

$R=CH_3$).

EXAMPLE 24

In the described fashion as in Example 15, replacing N-methylpiperazine in 15(g) with an appropriate amine such as ethylamine, ethanolamine, 1,2-diaminoethane, N-methylhydrazine, 3-hydroxymethyl-1-pyrrolidine, 3-methylaminopyrrolidine, 2-p-fluorophenyl-piperazine, 3-hydroxypyrrolidine, 3-aminomethyl-4-chloropyrrolidine, 2-methylpiperazine, or 3-aminomethyl-1-pyrrolidine, one can obtain the following compounds.

(a) 1-methyl-4-ethylamino-5-fluoro-1,2,8,9-tetrahydro-7H-isothiazolo[4',5':5,6]pyrido[1,2,3-de][1,4]benzoxazine-7,8-dione (I') ($Z=NHC_2H_5$ $R=CH_3$).

(b) 1-methyl-4-aminoethylamino-5-fluoro-1,2,8,9-tetrahydro-7H-isothiazolo[4',5':5,6]pyrido[1,2,3-de][1,4-]benzoxazine-7,8-dione (I') ($Z=NHC_2H_4NH_2$, $R=CH_3$).

(c) 1-methyl-4-hydroxyethylamino-5-fluoro-1,2,8,9-tetrahydro-7H-isothiazolo[4',5':5,6]pyrido[1,2,3-de][1,4-]benzoxazine-7,8-dione (I') ($Z=NHC_2H_4OH$, $R=CH_3$).

(d) 1-methyl-4-(3-hydroxymethyl-1-pyrrolidinyl)-5-fluoro-1,2,8,9-tetrahydro-7H-isothiazolo[4',5':5,6-]pyrido[1,2,3-de][1,4]benzoxazine-7,8-dione (I')

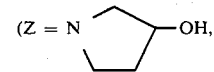

$R=CH_3$).

(e) 1-methyl-4-(2-methyl-1-hydrazyl)-5-fluoro-1,2,8,9-tetrahydro-7H-isothiazolo[4',5':5,6]pyrido[1,2,3-de][1,4]benzoxazine-7,8-dione (I') $Z=(NHNHCH_3$, $R=CH_3$).

(f) 1-methyl-4-(3-methylamino-1-pyrrolidinyl)-5-fluoro-1,2,8,9-tetrahydro-7H-isothiazolo[4',5':5,6-]pyrido[1,2,3-de][1,4]benzoxazine-7,8-dione (I')

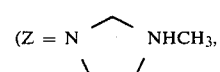

$R=CH_3$).

(g) 1-methyl-4-(3-p-fluorophenyl-1-piperzinyl)-5-fluoro-1,2,8,9-tetrahydro-7H-isothiazolo[4',5':5,6-]pyrido[1,2,3-de][1,4-benzoxazine-7,8-dione (I')

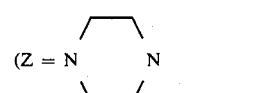

$R=CH_3$).

(h) 1-methyl-4-(3-hydroxy-1-pyrrolidinyl)-5-fluoro-1,2,8,9-tetrahydro-7H-isothiazolo[4',5':5,6]pyrido[1,2,3-de][1,4]benzoxazine-7,8-dione (I')

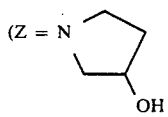

R=CH₃).

(i) 1-methyl-4-(3-aminomethyl-4-chloro-1-pyrrolidinyl)-5-fluoro-1,2,8,9-tetrahydro-7H-isothiazolo[4',5':5,6]pyrido[1,2,3-de][1,4]benzoxazine-7,8-dione (I')

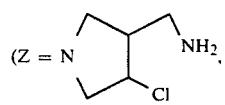

R=CH₃).

(j) 1-methyl-4-(3-methyl-1-piperazinyl)-5-fluoro-1,2,8,9-tetrahydro-7H-isothiazolo[4',5':5,6]pyrido[1,2,3-de][1,4-benzoxazine-7,8-dione (I')

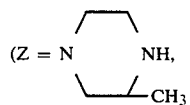

R=CH₃).

(k) 1-methyl-4-(3-aminomethyl-1-pyrrolidinyl)-5-fluoro-1,2,8,9-tetrahydro-7H-isothiazolo[4',5':5,6]pyrido[1,2,3-de][1,4]benzoxazine-7,8-dione (I')

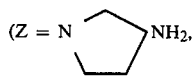

R=CH₃).

EXAMPLE 25

1-methylene-4-(4-methylpiperazinyl)-5-fluoro-1,2,8,9-tetrahydro-7H-isothiazolo[4',5':5,6]pyrido[1,2,3-de][1,4-]benzoxazine-7,8-dione (a) In the described fashion in Example 15(b) replacing methyl N-(2-chloro-1-methylethyl)iminochlorothioformate (4') (R₈=CH₃) with methyl N-(2-chloro-1-chloromethylethyl)iminochlorothioformate (4') (R₈=CH₂Cl) one can obtain the 1,4-dihydro-4-oxoquinoline-3-carboxylate (5') (R₉=C₂H₅, R₈=CH₂Cl).

(b) By following Example 15(c-f), the preceding compound (5') (R₉=C₂H₅, R₈=CH₂Cl) can yield 1-chloromethyl-4,5-difluoro-1,2,8,9-tetrahydro-7H-isothiazolo[4',5':5,6]pyrido[1,2,3:de][1,4]benzoxazine-7,8-dione (9') (R₈=CH₂Cl).

(c) In the described fashion as Example 15(g) displacing the 4-fluoro with N-methylpiperazine, the preceding compound (9') can yield 1-methylene-4-(4-methyl-1-piperazinyl)-5-fluoro-1,2,8,9-tetrahydro-7H-isothiazolo[4',5':5,6]pyrido[1,2,3-de][1,4]benzoxazine-7,8-dione (III').

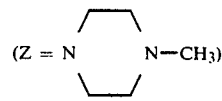

EXAMPLE 26

By following the example 25(a-c), replacing the N-methylpiperazine in 25(c) with various amines such as piperazine, 3-formamidopyrrolidine, piperidine, pyrrolidine, morpholine, thiomorpholine, homopiperazine, N-N-dimethylhydrazine, 2-methylpiperazine, 2-phenylpiperazine, 3-amino-4-methylpyrrolidine one can obtain the following compounds.

(a) 1-methylene-4-(1-piperazinyl)-5-fluoro-1,2,8,9-tetrahydro-7H-isothiazolo[4',5':5,6]pyrido[1,2,3-de][1,4-]benzoxazine-7,8-dione (III')

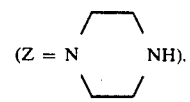

(b) 1-methylene-4-(3-formamido-1-pyrrolidinyl)-5-fluoro-1,2,8,9-tetrahydro-7H-isothiazolo[4',5':5,6-]pyrido[1,2,3-de][1,4]benzoxazine-7,8-dione (III')

(c) 1-methylene-4-(1-piperidinyl)-5-fluoro-1,2,8,9-tetrahydro-7H-isothiazolo[4',5':5,6]pyrido[1,2,3-de][1,4-]benzoxazine-7,8-dione (III')

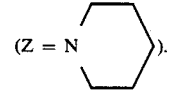

(d) 1-methylene-4-(1-pyrrolidinyl)-5-fluoro-1,2,8,9-tetrahydro-7H-isothiazolo[4',5':5,6]pyrido[1,2,3-de][1,4-benzoxazine-7,8-dione (III')

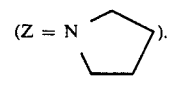

(e) 1-methylene-4-(1-morpholinyl)-5-fluoro-1,2,8,9-tetrahydro-7H-isothiazolo[4',5':5,6]pyrido[1,2,3-de][1,4-]benzoxazine-7,8-dione (III')

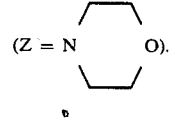

(f) 1-methylene-4-(1-thiomorpholinyl)-5-fluoro-1,2,8,9-tetrahydro-7H-isothiazolo[4',5':5,6]pyrido[1,2,3-de][1,4]benzoxazine-7,8-dione (III')

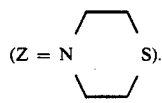

(g) 1-methylene-4-(1-homopiperazinyl)-5-fluoro-1,2,8,9-tetrahydro-7H-isothiazolo[4',5':5,6]pyrido[1,2,3-de][1,4]benzoxazine-7,8-dione (III')

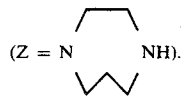

(h) 1-methylene-4-(1-N,N-dimethylhydrazyl)-5-fluoro-1,2,8,9-tetrahydro-7H-isothiazolo[4',5':5,6-]pyrido[1,2,3-de][1,4]benzoxazine-7,8-dione (III') (Z=NHN(CH$_3$)$_2$).

(i) 1-methylene-4-(3-methyl-1-piperazinyl)-5-fluoro-1,2,8,9-tetrahydro-7H-isothiazolo[4',5':5,6]pyrido[1,2,3-de][1,4]benzoxazine-7,8-dione (III')

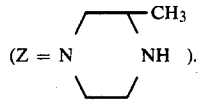

(j) 1-methylene-4-(3-phenyl-1-piperazinyl)-5-fluoro-1,2,8,9-tetrahydro-7H-isothiazolo[4',5':5,6]pyrido[1,2,3-de][1,4]benzoxazine-7,8-dione (III')

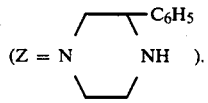

(k) 1-methylene-4-(3-amino-4-methyl-1-pyrrolidinyl)-5-fluoro-1,2,8,9-tetrahydro-7H-isothiazolo[4',5':5,6-]pyrido[1,2,3-de][1,4]benzoxazine-7,8-dione (III')

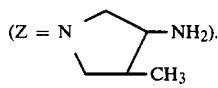

EXAMPLE 27

1-methylene-4-(3-amino-1-pyrrolidinyl)-5-fluoro-1,2,8,9-tetrahydro-7H-isothiazolo-[4',5':5,6]pyrido[1,2,3-de][1,4]benzoxazine-7,8-dione By following the procedure as Example (18), the product of Example 26(b) can be hydrolyzed to yield 1-methylene-4-(3-amino-1-pyrrolidinyl)-5-fluoro-1,2,8,9-tetrahydro-7H-isothiazolo[4',5':5,6]pyrido[1,2,3-de][1,4]benzoxazine-7,8-dione hydrochloride salt (III')

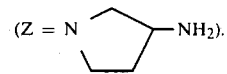

It will be understood that various changes and modifications can be made in the details of procedure, formulation and use without departing from the spirit of the invention, especially as defined in the following claims.

What is claimed is:

1. A compound having the formula

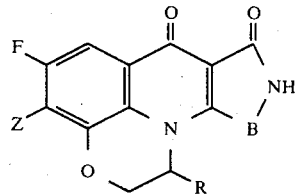

wherein B is selected from oxygen and sulfur, and R is $C_1$ to $C_4$ alkyl or =CH$_2$ and Z is selected from (a) a phenyl, (b) an amino group of the formula

wherein $R_1$ is hydrogen, $C_1$ to $C_4$ alkyl, amino-substituted $C_1$ to $C_4$ alkyl, hydroxy-substituted $C_1$ to $C_4$ alkyl, and $R_2$ is selected from the group consisting of $C_1$ to $C_4$ alkyl, hydroxy-substituted $C_1$ to $C_4$ alkyl, an amino group, a mono-($C_1$ to $C_4$) alkylamino group and a di-($C_1$ to $C_4$) alkylamino groups; (c) an aliphatic heterocyclic ring having the structure

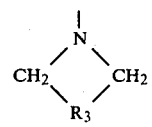

wherein $R_3$ is a group of formula —(CH$_2$)$_n$— wherein n is 2 or 3 or a group of the formula —(CH$_2$)$_n$—R$_4$—CH$_2$— wherein n is 1 or 2 and $R_4$ is selected from the group consisting of —S—, —O— and —NH—; substituted derivatives of the aliphatic heterocyclic ring substituted with one or more substituents selected from the group consisting of $C_1$ to $C_4$ alkyl, hydroxy-substituted $C_1$ to $C_4$ alkyl, hydroxy, amino-substituted $C_1$ to $C_4$ alkyl, phenyl, halophenyl, halogen, alkanoylamido containing 1 to 4 carbon atoms and an amino of the formula

wherein $R_5$ and $R_6$ are each independently selected from the group consisting of hydrogen, $C_1$ to $C_4$ alkyl; (d) a bicyclic heterocyclic ring having the formula

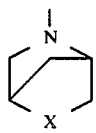

wherein X is selected from the group consisting of —S—, —O—, and —N—; and (e) bicyclic heterocyclic rings of the formula

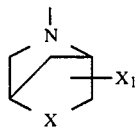

wherein $X_1$ is one or more of $C_1$ to $C_4$ alkyl, hydroxy-substituted $C_1$ to $C_4$ alkyl, phenyl, halophenyl, amino-substituted $C_1$ to $C_4$ alkyl, hydroxy, halogen, alkanoylamido having 1 to 4 carbon atoms, an an amino of the formula

and pharmaceutically acceptable salts thereof.

2. The compound as defined in claim 1 wherein Z is selected from the group consisting of piperazinyl groups, piperidinyl groups, pyrrolidinyl groups, morpholino groups, thiomorpholino groups, homopiperazinyl groups and substituted derivatives thereof.

3. A compound defined in claim 1 wherein B is oxygen; R is methyl, and Z is piperazinyl, 4-methyl-1-piperazinyl, 3-amino-1-pyrrolidinyl, 3-methyl-1-piperazinyl, 3-amino-4-methyl-1-pyrrolidinyl, 3-aminomethyl-1-pyrrolidinyl or 3-ethylaminomethyl-1-pyrrolidinyl.

4. A compound defined in claim 1 wherein B is oxygen; R is methylene, Z is piperazinyl, 4-methyl-1-piperazinyl, 3-methyl-1-piperazinyl, 3-amino-1-pyrrolidinyl or 3-amino-4-methyl-1-pyrrolidinyl.

5. A compound defined in claim 1 wherein B is sulfur; R is methyl; and Z is piperazinyl, 4-methyl-1-piperazinyl 3-amino-1-pyrrolidinyl, 3-methyl-1-piperazinyl, 3-amino-4-methyl-1-pyrrolidinyl, 3-aminomethyl-1-pyrrolidinyl or 3-ethylaminomethyl-1-pyrrolidinyl.

6. A compound defined in claim 1 wherein B is sulfur; R is methylene and Z is piperazinyl, 4-methyl-1-piperazinyl, 3-methyl-1-piperazinyl, 3-amino-1-pyrrolidinyl, 3-amino-4-methyl-1-pyrrolidinyl.

7. A composition having antibacterial activity in pharmaceutical dosage form containing a diluent and a compound as defined in claim 1.

8. A method of treating a bacterial infection in a patient comprising administering to a patient in need of such treatment a therapeutically effective amount of a compound as defined in claim 1.

* * * * *